United States Patent [19]

Jequier et al.

[11] 4,283,577

[45] Aug. 11, 1981

[54] METHOD FOR MAKING ETHYLENE CHLOROHYDRIN

[75] Inventors: William Jequier, Beauvais; Elie Ghenassia, Bethune; Francois Fine, Saint Laurent de Mure; Gerard Krempf, Sainte-Foy-les-Lyon, all of France

[73] Assignee: Produits Chimiques Ugine Kuhlmann, Courbevole, France

[21] Appl. No.: 71,676

[22] Filed: Aug. 31, 1979

[30] Foreign Application Priority Data

Sep. 29, 1978 [FR] France ............................ 78 27892

[51] Int. Cl.$^3$ ............................................. C07C 31/34
[52] U.S. Cl. .................................. 568/841; 568/614; 568/676
[58] Field of Search .................................. 568/841

[56] References Cited

U.S. PATENT DOCUMENTS

| | | | |
|---|---|---|---|
| 1,954,395 | 4/1934 | Stampe | 568/841 X |
| 2,636,906 | 4/1953 | Davis | 568/841 |

FOREIGN PATENT DOCUMENTS 968902 4/1958 Fed. Rep. of Germany .
422241 1/1976 U.S.S.R. .

OTHER PUBLICATIONS

Parausanu et al., Chem. Abs. 74, 1971, 99387u, Revista de Chimie (Bucharest) vol. 21, pp. 743-746.
Ullmanns, Encyclopedie der technischen Chemie, Urban & Schwarzenberg, Mar. 1953, vol. 3, p. 131.
Hartmann, Theoretica Chemica Acta, 51, No. 1, 1979, 11-35.
Repas et al., Chem. Prumysl:10, 238-240, 1960, CA, 54, 1960, 24376b.

*Primary Examiner*—Howard T. Mars
*Attorney, Agent, or Firm*—Sigalos & Levine

[57] ABSTRACT

This invention relates to the method for making ethylene oxide, characterized by the fact that ethylene oxide in the gaseous state is made to react with anhydrous gaseous hydrochloric acid, with the reaction medium likewise being maintained in the gaseous state during the reaction.

5 Claims, 1 Drawing Figure

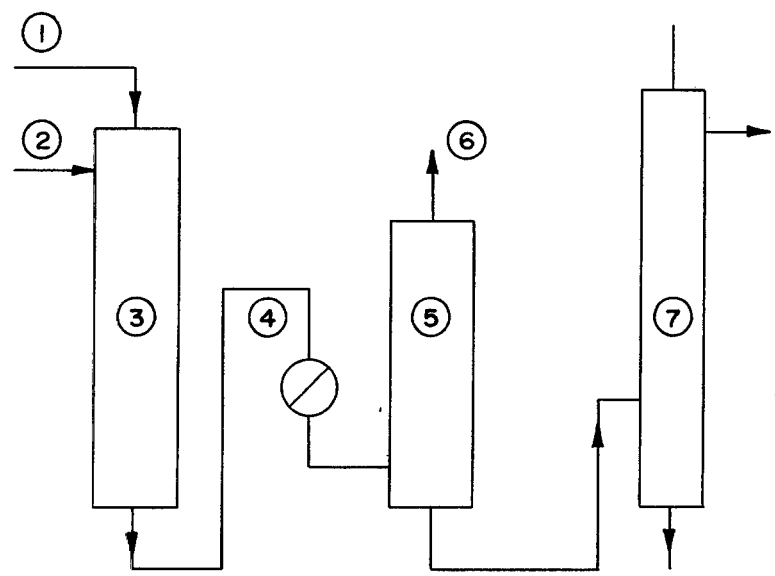

METHOD FOR MAKING ETHYLENE CHLOROHYDRIN

BACKGROUND OF THE INVENTION

Ethylene chlorohydrin, an intermediate product used in the manufacture of polysulfide elastomers, such as the "Thiokols," is also utilized in the synthesis of certain pesticides, paints, and varnishes, and as a solvent in the preparation of cellulose acetate. There are several known methods for the preparation of ethylene chlorohydrin, none of which are entirely satisfactory.

One method for the preparation of ethylene chlorohydrin from ethylene and chlorine in aqueous medium is described in French Pat. No. 1,511,682. This method presents the drawback of yielding a dilute solution, from which it is difficult and costly to extract the ethylene chlorohydrin in anhydrous (dry) form because of the formation of an azeotrope containing 58% of water and 42% of ethylene chlorohydrin and having a boiling point of 97.8° C.

Another technique for the preparation of ethylene chlorohydrin, described in German Patent No. 968,902, consists of passing a gas containing ethylene oxide into some ethylene chlorohyrin saturated with hydrochloric acid. This manner of operating results in the formation of higher products (in the series): diethylene glycol chlorohydrin (CHDEG) $CH_2OH—CH_2—O—CH_2—CH_2Cl$ and triethylene glycol chlorohydrin (CHTEG) $CH_2OH—CH_2—O—CH_2—CH_2—O—CH_2—CH_2Cl$; and therefore the yield in ethylene chlorohydrin (CHEG) does not exceed 80–90%.

Russian inventor's Certificate No. 422,241 discusses the method for the preparation of ethylene chlorohydrin by reaction, in the liquid phase, of ethylene oxide with previously purified hydrochloric acid and cites the drawbacks of this method. According to the technique described in this Russian inventor's Certificate No. 422,241, the disadvantages of this method are remedied by having ethylene oxide and moist (wet) hydrochloric acid react in the presence of an organosilane. However, this method does not permit a yield exceeding 88–92% of ethylene chlorohydrin.

SUMMARY OF THE INVENTION

The present invention overcomes the drawbacks encountered in the techniques of the prior art and results in obtaining a minimum molar yield of 95% in pure ethylene chlorohydrin, based on the ethylene oxide, and a minimum yield, by weight, amounting to 97%, with the conversion ratio of the ethylene oxide reaching 100%.

Briefly stated, the present invention comprises the method of making ethylene chlorohydrin comprising forming a reaction mixture comprising ethylene oxide in a gaseous state and anhydrous, gaseous hydrochloric acid and maintaining the reaction mixture in a gaseous state during the reaction period.

BRIEF DESCRIPTION OF THE DRAWING

The sole FIGURE of the drawing is a schematic view of a reaction cycle and an apparatus system that can be used to carry out the method of the present invention.

DETAILED DESCRIPTION

The present invention concerns a method for the preparation of ethylene chlorohydrin, or 2-chloroethanol-1, having the formula $ClCH_2—CH_2OH$, from ethylene oxide and hydrochloric acid under such conditions that the excess hydrochloric acid and the ethylene chlorohydrin formed remain in the gaseous state in the reactor during the reaction.

A satisfactory and practical way of carrying out the present method is to vaporize the ethylene oxide prior to it entering the reactor by passing it through a vaporizer or through a vaporization zone before entering into contact with the hydrochloric acid. Under these conditions, the temperature of the ethylene oxide is found to be at a temperature between 50° and 180° C., and preferably between 50° and 120° C. Likewise, the pure and dry hydrochloric acid is introduced into the reactor as a gas (hydrogen chloride) at a temperature between 50° and 180° C., and preferably between 50° and 120° C. The hydrochloric acid can be allowed to react in concentrated form or in diluted form in an inert gas such as, for instance, nitrogen, carbon dioxide, or helium. While the dilution of the hydrochloric acid in an inert gas does not affect the successful application of the method at all, it does, however, permit the utilization, as is, of the mixture of hydrochloric acid and inert gas obtained, for instance, from the synthesis of hydrogen chloride using chlorine burners.

The reaction of ethylene oxide with hydrochloric acid generally is carried out at a temperature in the reactor of between 130° and 300° C., preferably between 130° and 250° C. and at such a pressure that the ethylene chlorohydrin having been formed remains in the gaseous form. This utilization pressure is a function of the temperature ranges and of the molar ratios which have been envisioned and is determined by the dew point of the gas mixtures coming out of the reactor; that is to say, for a pressure range below 20 bars.

The molar ratio of hydrochloric acid to ethylene oxide is selected as a function of the desired productivity. It can vary within a wide range and does not affect either the selectivity of the yield of the reaction calculated on the basis of the ethylene oxide. It is, however, attractive to utilize such a molar ratio that by a simple heating of the mass, the hydrochloric acid excess plays the role of reaction regulator by eliminating the heat generated by said reaction, in such a way as to obtain the appropriate temperature so that the reactor can function under adiabatic conditions. In practice, the molar ratio of the hydrochloric acid to the ethylene oxide can vary from stoichiometrically equal proportions to 40:1, but it is advised to operate between 2:1 and 20:1 and, better still, between 2:1 and 10:1.

The method can likewise function under semi-isothermal conditions in a reactor equipped with a device for heat evacuation by water evaporation followed by recovery of the heat having been produced.

According to a preferred mode of carrying out the method of the instant invention, the ethylene chlorohydrin can be obtained using the reaction cycle and apparatus system shown in schematic form in the drawing. The preheated anhydrous gaseous hydrochloric acid and the preheated gaseous ethylene oxide are respectively introduced in cocurrent flow through tubes 1 and 2 into reactor 3, of the standard known type, at the selected reaction temperature and pressure. The ethylene chlorohydrin in the gaseous state and the hydrochloric acid, more or less in excess, coming out of the reactor are cooled by passing over a heat exchanger 4, then collected in a separation column or a condenser 5, from which the fraction of hydrochloric acid insoluble in ethylene chlorohydrin is eliminated through tube 6. The mixture of dissolved hydrogen chloride and ethylene chlorohydrin then passes into a distillation column 7, from which the pure ethylene chlorohydrin is extracted after the hydrochloric acid has been expelled from it, with the high-molecular-weight products being recovered at the bottom of the column. The gaseous hydrochloric acid recovered during the purification stages of the ethylene chlorohydrin can be recycled to the reactor at 1.

The invention will be further described in connection with the following examples which are given for purposes of illustration only.

EXAMPLE 1

In a glass tube, with a double jacket, having an internal diameter of 45 mm. and a length of 590 mm., filled with RASCHIG rings made of sandstone (6×6), with the effective volume amounting to 345 cm$^3$, 93 grams/hour of gaseous ethylene oxide having previously been passed through a vaporizer at 50° C. and 274 grams/hour of dry gaseous hydrochloric acid having been preheated to 50° C. are allowed to arrive in cocurrent flow through the upper part of the reactor. The temperature in the reactor is kept at 155°–160° C. with the help of the circulation of a coolant, making it possible to eliminate the heat of the reaction. The reactor is operated at atmospheric pressure, with the time the reagents remain in contact amounting to 3.6 seconds.

After passage into a condenser kept at 17° C., there is recovered a mixture containing 166.8 g. of crude chlorohydrin and 26.0 g. of dissolved hydrochloric acid; 174 g. of HCl are eliminated at the top (head) of the condenser.

Chromatographic analysis of the crude chlorohydrin after stripping of the dissolved HCl at 100°–110° C. yields the following weight distribution: 161.6 g. of ClCH$_2$—CH$_2$OH, 3.5 g. of CH$_2$CL—CH$_2$—O—CH$_2$—CH$_2$OH and 1.7 g. of CH$_2$Cl—CH$_2$—O—CH$_2$—CH$_2$—O—CH$_2$—CH$_2$OH. The conversion ratio of ethylene oxide into ethylene chlorohydrin amounts to 96.5%, and to 3.5% into the higher products CHDEG and CHTEG. The conversion of the ethylene oxide is a (100%) total conversion.

EXAMPLE 2

The same apparatus set-up as in Example 1 is used at atmospheric pressure, with the contact time of the reagents being 3.6 seconds and the molar ratio of HCl/ethylene oxide being 9:1 as opposed to the 3.6:1 ratio of Example 1.

44.8 grams/hour of gaseous ethylene oxide having been preheated to 60° C. and 338 grams/hour of gaseous and dry hydrochloric acid (hydrogen chloride) at 60° C. are allowed to arrive in the reactor in cocurrent flow. The temperature in the reactor is kept at 133°–136° C., by eliminating the heat produced with the help of a coolant.

After passage into a condenser kept at 18° C., there is recovered a mixture containing 81.4 g. of crude chlorohydrin and 12.7 g. of dissolved HCl. After elimination of the dissolved HCl by heating, chromatographic analysis yields 72.8 g. of ethylene chlorohydrin, 1.86 g. of CHDEG and 0.73 g. of CHTEG. The conversion ratio of ethylene oxide into ethylene chlorohydrin amounts to 95.8%.

EXAMPLE 3

In a heat-insulated reactor, consisting of an empty tube having a length of 250 mm., a diameter of 22 mm., and a volume of 94 cm$^3$, 52.9 grams/hour of gaseous ethylene oxide, 395 grams/hour of gaseous and dry hydrochloric acid and 42 grams/hour of nitrogen are sent through the upper part of the reactor in cocurrent flow, all three of the gases having been preheated to 60° C. The temperature reached in the reactor without the help of any external heating arrangement is 162° C. By operating under atmospheric pressure, the reaction is practically instantaneous. The molar ratio used amounts to 9:1.

After passage into a condenser kept at 25° C., 96.3 g. of crude chlorohydrin and 15.1 g. of dissolved HCl are collected. The gaseous mixture of N$_2$ and HCl leaving at the top (head) of the condenser, after having been neutralized with an alkaline solution, contains 336.5 g. of hydrochloric acid. The determination of the crude ethylene chlorohydrin, after the HCl has been eliminated, yields 94.4 g. of CHEG, (ethylene chlorohydrin), 1.7 g. of CHDEG and 0.15 g. of CHTEG. The conversion ratio of ethylene oxide into ethylene chlorohydrin amounts to 97.6% and the conversion ratio into higher products amounts to 2.4%. Conversion of the ethylene oxide reaches 100%.

EXAMPLE 4

In the same apparatus set-up as the one utilized in Example 2, 69.4 grams/hour of gaseous ethylene oxide, 380 grams/hour of gaseous and dry hydrochloric acid and 47 grams/hour of nitrogen are sent into the reactor in cocurrent flow, with the gases having been preheated to 60° C. The temperature reached in the reactor, without the help of any external heating arrangement, amounts to 160° C. The molar ratio of HCl/ethylene oxide is 6.6:1 and the reaction time is identical to the one used in Example 3; namely, 0.7 seconds. The reactor is operated under atmospheric pressure.

After passage into a condenser kept at 25° C., 147.3 g. of a mixture containing 125.8 g. of crude ethylene chlorohydrin and 21.5 g. of dissolved HCl are obtained. The gaseous mixture of N$_2$+HCl leaving at the top (head) of the condenser contains 302.3 g. of HCl. The chromatographic analysis of the crude chlorohydrin yields 121.9 g. of pure ethylene chlorohydrin, 3.5 g. of CHDEG and 0.4 g. of CHTEG. The conversion ratio into CHEG based on ethylene oxide amounts to 96% and the conversion ratio into higher products amounts to 4%. Conversion of the ethylene oxide is 100% complete.

EXAMPLE 5

In a practically adiabatic reactor consisting of an hollow tube having a diameter of 29 mm. and a length of 600 mm., 66.1 grams/hour of gaseous ethylene oxide, 378 grams/hour of recycled gaseous hydrochloric acid, and 28 grams/hour of nitrogen are introduced in cocurrent flow through the upper part of the reactor and at atmospheric pressure, with the reagents having been preheated to 60° C.

The temperature reached in the reactor amounts to 152° C. below the introduction zone of the reagents and to 174°–180° C. in the remainder of the reaction zone. The molar ratio amounts to 6.8:1 and the reaction time to 3 seconds.

After passage into a condenser at 25° C., 141 g. of a mixture containing 120 g. of crude ethylene chlorohydrin and 21 g. of dissolved HCl are obtained, with the N₂—HCl mixture coming out at the head (top) of the condenser containing 299.1 g. of hydrochloric acid. An analysis of the crude chlorohydrin by chromatography yields 47.2 g. of pure chlorohydrin, 2.2 g. of CHDEG and 0.6 g. of CHTEG. The conversion ratio into ethylene chlorohydrin based on ethylene oxide amounts to 96.9% and the conversion ratio into higher products amounts to 3.1%

EXAMPLE 6

The reactor used in Example 5 is filled with RASCHIG rings, 5×5, for the purpose of perfecting the gas-gas contact. The effective volume of the reactor then becomes 240 cm³.

92 grams/hour of gaseous ethylene oxide, 572 grams/hour of recycles dry, gaseous hydrochloric acid and 63 grams/hour of nitrogen are introduced in cocurrent flow through the upper part of the reactor at atmospheric pressure. The reagents are preheated to 60° C. The temperature reached in the reactor amounts to 138° C. below the introduction zone and to 197°-200° C. in the remainder of the reaction zone. The molar ratio amounts to 7.4:1 and the reaction time to 1.2 seconds.

After passage into a condenser at 25° C., 194.2 g. of a mixture containing 167.8 g. of crude chlorohydrin and 26.4 g. of dissolved hydrochloric acid are obtained. An analysis of the crude chlorohydrin yields 163.9 g. of pure ethylene chlorohydrin, 3 g. of diethylene chlorohydrin and 0.9 g. of triethylene chlorohydrin. The conversion ratio of ethylene oxide into ethylene chlorohydrin amounts to 97.4%.

EXAMPLE 7

In the reactor of Example 6, by starting with 72.9 grams/hour of gaseous ethylene oxide and operating with a molar ratio of HCl/ethylene oxide of 8.85:1 at a temperature of 182°-186° C., the conversion ratio of ethylene oxide into ethylene chlorohydrin reaches 97.3% for a total conversion of the ethylene oxide. The reagents are introduced in cocurrent through the upper part of the reactor while operating under atmospheric pressure, with the contact time being 1.5 seconds.

EXAMPLE 8

The same equipment set-up as in Example 2 is used, with the preheating temperature being raised to 120° C. The same quantities of gaseous ethylene oxide and hydrochloric acid are introduced. The temperature is kept at 180° C. with the help of the circulation of a coolant. The yields are in all points comparable to those of Example 2.

EXAMPLE 9

Into a pipe of ordinary steel having an internal diameter of 21.2 mm. and a length of 300 mm., the same quantities of gaseous ethylene oxide and gaseous hydrochloric acid are introduced as were used in Example 2, but under a pressure of 15 bars and each preheated to 120° C. The temperature of the reactor is kept at 180° C. with the help of the circulation of a coolant. The yields are in all points comparable to those of Example 2.

EXAMPLE 10

Into a pipe of ordinary steel having been carefully insulated against heat loss, consisting of a hollow tube having a length of 250 mm. and a diameter of 21.2 mm., the same quantities of gaseous ethylene oxide and gaseous hydrochloric acid are sent in cocurrent flow as in Example 3. Preheating is likewise kept at 60° C. The reaction is carried out at an absolute pressure of 3 bars. The yields are in all points comparable to those of Example 3.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. The method of making ethylene chlorohydrin comprising forming a reaction mixture of gaseous ethylene oxide and anhydrous, gaseous hydrochloric acid and maintaining the reaction mixture in a gaseous state at a temperature of from about 130° to 300° C. during the reaction period.

2. The method of claim 1 wherein the temperature of the gaseous ethylene oxide and of the gaseous hydrochloric acid used to form the reaction mixture is from about 50° to 180° C.

3. The method of claim 1 or 2 wherein the molar ratio of hydrochloric acid to ethylene oxide is from stoichiometric equivalents to 40:1.

4. The method of claim 1 or 2, wherein the reaction is carried out at a pressure from atmospheric pressure to about 20 bars.

5. The method of making ethylene chlorohydrin comprising introducing gaseous ethylene oxide and anhydrous, gaseous hydrochloric acid, each at a temperature of from about 50° to 120° C., into a reaction zone to form a reaction mixture, maintaining the reaction mixture at a temperature of from about 130° to 250° C. and at atmospheric pressure for a time sufficient for the reaction to be substantially completed, and separating ethylene chlorohydrin from the reaction mixture; the molar ratio of hydrochloric acid to ethylene oxide introduced to the reaction zone being from 2:1 to 20:1.

* * * * *